(12) United States Patent
Welniak et al.

(10) Patent No.: US 9,146,404 B1
(45) Date of Patent: Sep. 29, 2015

(54) LASER-X RADIATION/LASER COMBO PROTECTIVE EYEWEAR SYSTEM

(76) Inventors: Kevin Welniak, Lutz, FL (US); Ryan Phillips, Middlesex, NJ (US)

( * ) Notice: Subject to any disclaimer, the term of this patent is extended or adjusted under 35 U.S.C. 154(b) by 185 days.

(21) Appl. No.: 13/400,433

(22) Filed: Feb. 20, 2012

(51) Int. Cl.
*G02C 7/10* (2006.01)
*G02C 7/02* (2006.01)

(52) U.S. Cl.
CPC ..................................... *G02C 7/022* (2013.01)

(58) Field of Classification Search
USPC ...................... 351/44, 49, 41, 159.57, 159.49; 359/350, 499
See application file for complete search history.

(56) References Cited

U.S. PATENT DOCUMENTS 5,668,618 A * 9/1997 Simioni ........................... 351/44
6,637,877 B1 * 10/2003 Hartley et al. .................. 351/44

* cited by examiner

*Primary Examiner* — Hung Dang

(57) ABSTRACT

A primary lens element fabricated of laser protective glass has proximal and distal faces, a central extent and a peripheral extent. A secondary lens element fabricated of lead oxide has proximal and distal faces, a central extent and a peripheral extent. The secondary lens is operatively coupled to the primary lens forming a lens laminate ground to form a composite lens with a prescription. The composite lens has a central extent of an enlarged thickness and a peripheral extent of a reduced thickness.

11 Claims, 2 Drawing Sheets

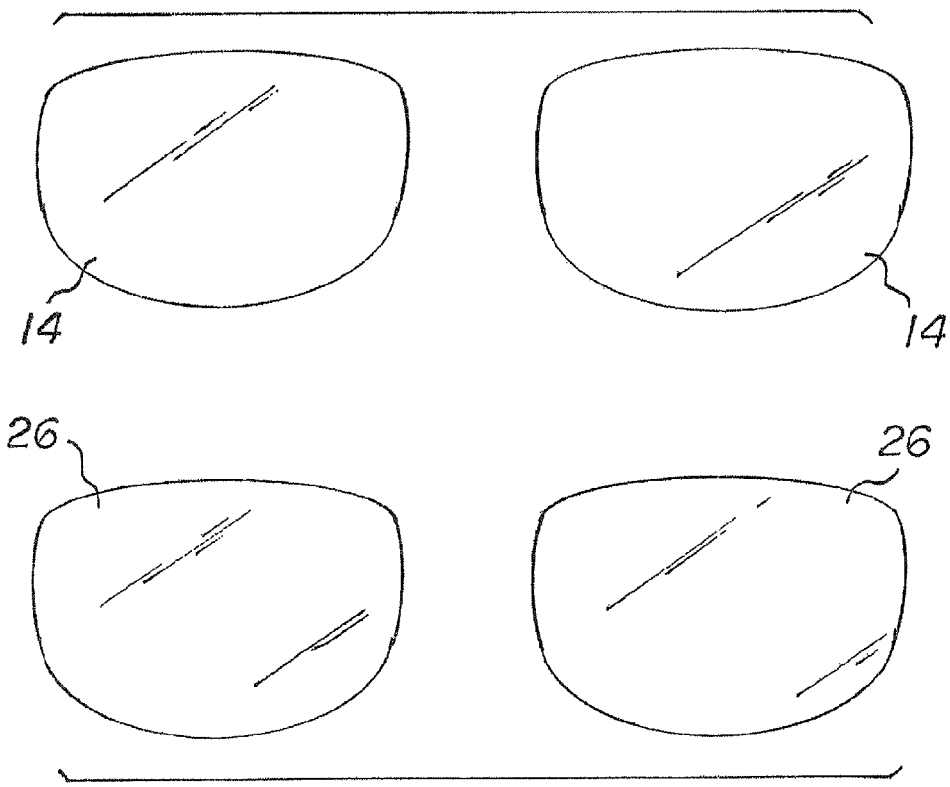

LASER-X RADIATION/LASER COMBO PROTECTIVE EYEWEAR SYSTEM

BACKGROUND OF THE INVENTION

Field of the Invention

The present invention relates to a laser-x radiation/laser combo protective eyewear system and more particularly pertains to abating, through safety filtration, the harmful effects to eyes of a user from laser radiation and from radiation from fluoroscopy imaging procedures, the abating, through safety filtration, of the harmful radiation effects being done in a safe, convenient and economic manner.

SUMMARY OF THE INVENTION

In view of the disadvantages inherent in the known types of sunglass systems of known designs and configurations now present in the prior art, the present invention provides an improved laser-x radiation/laser combo protective eyewear system. As such, the general purpose of the present invention, which will be described subsequently in greater detail, is to provide a new and improved laser-x radiation/laser combo protective eyewear system and method which has all the advantages of the prior art and none of the disadvantages.

To attain this, the present invention essentially comprises a laser-x radiation/laser combo protective eyewear system. First provided are two primary lens elements. Each primary lens element has a proximal face. Each primary lens element has a planar distal face. Each primary lens has a central region. Each primary lens also has a peripheral region. Each primary lens element is fabricated of laser protective glass. The laser protective glass has laser glass protective ranges of 900 nm to 950 nm at 4+ OD and 80 percent visibility L-6 rating, and 950 nm to 1000 nm at 5+ OD and 80 percent visibility L-6 rating, 1000 nm to 2400 nm at 6+ OD and 80 percent visibility L-6 rating, 2750 nm to 10600 nm at 7+OD and 80 percent visibility L-6 rating. Each primary lens is adapted to protect the eyes of the user from harmful effects of laser radiation.

Two secondary lens elements are provided. Each secondary lens element has a proximal face. Each secondary lens element has a planar distal face. Each secondary lens element has a central region. Each secondary lens element has a peripheral region. Each secondary lens element is fabricated of lead oxide glass. The lead oxide glass has a lead content of a minimum of 0.75 percent lead plus or minus 5 percent in a 1.80 high-index rate of refraction. The secondary lens is adapted to protect the eyes of the user from harmful effects of fluoroscopy radiation.

Each secondary lens element is operatively coupled to an associated primary lens element. In this manner two lens laminates are formed. The distal face of each primary lens forms a planar interface with each proximal face of an associated secondary lens.

Each proximal face of each primary lens and each distal face of each secondary lens is ground. In this manner two composite lenses are formed. The composite lenses have a minimum prescription. Also in this manner each composite lens has a central region of an enlarged thickness. Further in this manner each composite lens has a peripheral region of a reduced thickness less than the thickness of the central extent.

Further provided is a frame. The frame has a front section. The front section receives and supports a pair of composite lenses in an essentially common front plane. The frame has side sections. The side sections extend proximally and positionable over ears of the user. The composite lenses are positioned in the frame. The primary lens elements are located proximally of the secondary lens elements.

Provided last are supplemental composite lenses. The supplemental lenses are positioned in the front section adjacent to the side sections. The supplemental lenses are in essentially parallel side planes perpendicular to the front plane. The supplemental composite lenses are adapted to provide lateral vision free from the effects of laser and fluoroscope radiation, the supplemental lenses having slightly different curves to compensate for the refractive index of the refractive glass.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved laser-x radiation/laser combo protective eyewear system which has all of the advantages of the prior art sunglass systems of known designs and configurations and none of the disadvantages.

It is another object of the present invention to provide a new and improved laser-x radiation/laser combo protective eyewear system which may be easily and efficiently manufactured and marketed.

It is further object of the present invention to provide a new and improved laser-x radiation/laser combo protective eyewear system which is of durable and reliable constructions.

An even further object of the present invention is to provide a new and improved laser-x radiation/laser combo protective eyewear system which is susceptible of a low cost of manufacture with regard to both materials and labor, and which accordingly is then susceptible of low prices of sale to the consuming public, thereby making such laser-x radiation/laser combo protective eyewear system economically available to the buying public.

Even still another object of the present invention is to provide a laser-x radiation/laser combo protective eyewear system for abating, through safety filtration, the harmful effects to eyes of a user from laser radiation and from radiation from fluoroscopy imaging procedures, the abating, through safety filtration, of the harmful radiation effects being done in a safe, convenient and economic manner.

Lastly, it is an object of the present invention to provide a new and improved laser-x radiation/laser combo protective eyewear system. A primary lens element has proximal and distal faces, a central extent and a peripheral extent. The primary lens element is fabricated of laser protective glass. A secondary lens element has proximal and distal faces, a central extent and a peripheral extent. The secondary lens is fabricated of lead oxide glass. The secondary lens is operatively coupled to the primary lens. In this manner a lens laminate is formed. The lens laminate is ground to form a composite lens with a prescription. In this manner the composite lens has a central extent of an enlarged thickness and a peripheral extent of a reduced thickness less than the thickness of the central extent.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a front elevational view of lenses, front and back, of a laser-x radiation/laser combo protective eyewear system constructed in accordance with the principles of the present invention.

FIG. 2 is a cross sectional view of a lens constructed in accordance with the prior art.

FIGS. 3 and 4 are cross sectional views of the lenses of FIG. 1.

The same reference numerals refer to the same parts throughout the various Figures.

DESCRIPTION OF THE PREFERRED EMBODIMENT

Figure 5:
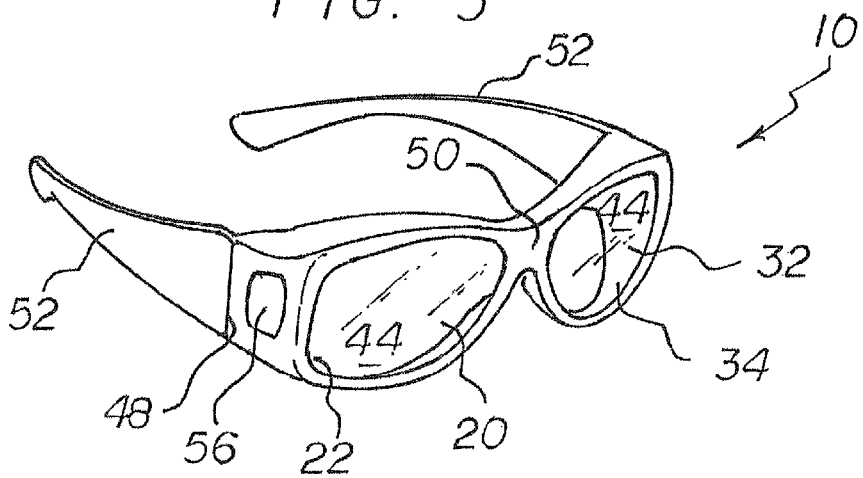
FIGS. 5, 6 and 7 are perspective illustrations of glasses utilizing the lenses of the prior Figures.
Figure 6:
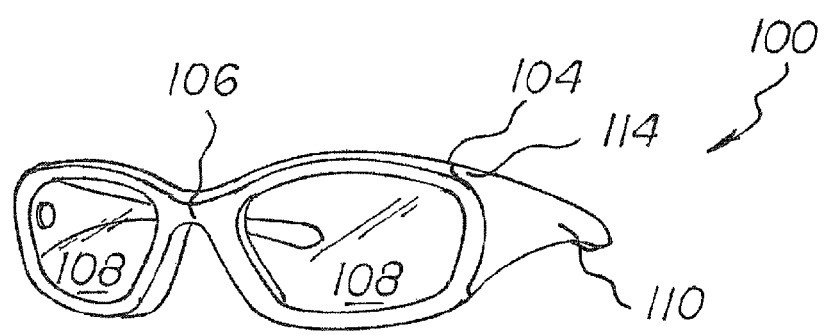
Figure 7:
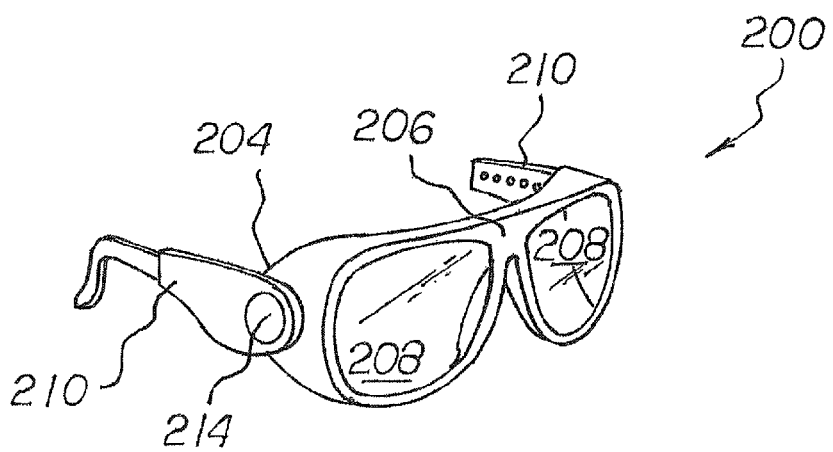

With reference now to the drawings, and in particular to FIG. 1 thereof, the preferred embodiment of the new and improved laser-x radiation/laser combo protective eyewear system embodying the principles and concepts of the present invention and generally designated by the reference numeral 10 will be described.

The present invention, the laser-x radiation/laser combo protective eyewear system 10 is comprised of a plurality of components. Such components in their broadest context include a primary lens and a secondary lens. Such components are individually configured and correlated with respect to each other so as to attain the desired objective.

First provided are two primary lens elements 14. Each primary lens element has a proximal face 16. Each primary lens element has a planar distal face 18. Each primary lens has a central region 20. Each primary lens also has a peripheral region 22. Each primary lens element is fabricated of laser protective glass. The laser protective glass has laser glass protective ranges of 900 nm to 950 nm at 4+ OD and 80 percent visibility L-6 rating, and 950 nm to 1000 nm at 5+ OD and 80 percent visibility L-6 rating, 1000 nm to 2400 nm at 6+ OD and 80 percent visibility L-6 rating, 2750 nm to 10600 nm at 7+OD and 80 percent visibility L-6 rating. Each primary lens is adapted to protect the eyes of the user from harmful effects of laser radiation.

Two secondary lens elements 26 are provided. Each secondary lens element has a proximal face 28. Each secondary lens element has a planar distal face 30. Each secondary lens element has a central region 32. Each secondary lens element has a peripheral region 34. Each secondary lens element is fabricated of lead oxide glass. The lead oxide glass has a lead content of a minimum of 0.75 percent lead plus or minus 5 percent in a 1.80 high-index rate of refraction. The secondary lens is adapted to protect the eyes of the user from harmful effects of fluoroscopy radiation.

Each secondary lens element is operatively coupled to an associated primary lens element. In this manner two lens laminates 38 are formed. The distal face of each primary lens forms a planar interface 40 with each proximal face of an associated secondary lens.

Each proximal face of each primary lens and each distal face of each secondary lens is ground. In this manner two composite lenses 44 are formed. The composite lenses have a minimum prescription. Also in this manner each composite lens has a central region of an enlarged thickness. Further in this manner each composite lens has a peripheral region of a reduced thickness less than the thickness of the central extent.

Further provided is a frame 48. The frame has a front section 50. The front section receives and supports a pair of composite lenses in an essentially common front plane. The frame has side sections 52. The side sections extend proximally and positionable over ears of the user. The composite lenses are positioned in the frame. The primary lens elements are located proximally of the secondary lens elements.

Provided last are supplemental composite lenses 56. The supplemental lenses are positioned in the front section adjacent to the side sections. The supplemental lenses are in essentially parallel side planes perpendicular to the front plane. The supplemental composite lenses are adapted to provide lateral vision free from the effects of laser and fluoroscope radiation.

An alternate embodiment 100 of the present invention is provided. A frame 104 is provided. The frame has a front section 106. The frame receives and supports a pair of composite lenses 108. The composite lenses are received and supported in an essentially common front plane. The frame has side sections 110. The side sections extend proximally and are positionable over ears of the user.

Hinges 114 are provided. The hinges are in a vertical plane. The hinges couple the front and side sections.

Another alternate embodiment 200 of the present invention is provided. A frame 204 is provided. The frame has a front section 206. The front section receives and supports a pair of composite lenses 208. The lenses are received and supported in an essentially common front plane. The frame has side sections 210. The side sections extend proximally and are positionable over ears of the user.

Hinges 214 are provided. The hinges are in a horizontal plane. The hinges couple the front and side sections.

To get laser and radiation protection in a single protective lens, it is first necessary to laminate laser protective glass to leaded oxide glass. Leaded oxide glass protects a user's eyes against certain injurious radiation and laser wave-lengths. Lead oxide protective glass protects the user's eyes against damage due to radiation emitted during interventional fluoroscopy radiation imaging. Interventional fluoroscopy radiation is an interventional imaging procedure where a laser may also utilized. Both laser and fluoroscopy radiation can injure the unprotected eye. Therefore, the eyes must protected from both radiation and laser.

Damage to the eye by radiation such as fluoroscopy, lasers and other radiation is both linear and cumulative. Laser injury to the eye can be instantaneously injurious and irreversible. Both laser and radiation injuries to the eye are generally accepted as being permanent. Until now, the laminated glass had to be made "flat" and "bulky" due to the fact that when the laminated glass is curved, it creates "distortion" such that nothing viewed through the glass may be viewed with any acceptability. The different indexes of refraction are the cause of the distortion.

With the Laser-X system of the present invention, lenses of laminated glass lens are ground into a very minimal prescription eye protection. To compensate for the different indexes, the lenses can then be fitted into acceptable and stylish eyewear frames with an acceptable field of vision and optical acuity.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A protective lens comprising:
    a primary lens element having proximal and distal faces and a central extent and a peripheral extent, the primary lens element being fabricated of laser protective glass;
    a secondary lens element having proximal and distal faces and a central extent and a peripheral extent, the secondary lens being fabricated of lead oxide glass;
    the secondary lens being operatively coupled to the primary lens to form a lens laminate; and
    the lens laminate being ground to form a composite lens with a prescription whereby the composite lens has a central extent of an enlarged thickness and a peripheral extent of a reduced thickness less than the thickness of the central extent.

2. The system as set forth in claim 1 wherein the secondary lens element is distally of the primary lens element.

3. The system as set forth in claim 1 wherein the secondary lens element is proximally of the primary lens element.

4. The system as set forth in claim 1 wherein the distal face of the secondary lens is ground and the proximal face of the primary lens is ground.

5. The system as set forth in claim 1 wherein the distal face of the secondary lens is ground.

6. The system as set forth in claim 1 wherein the proximal face of the primary lens is ground.

7. The system as set forth in claim 1 wherein the distal face of the primary lens and the proximal face of the secondary lens are planar.

8. The system as set forth in claim 1 and further including:
    a frame having a front section receiving and supporting a pair of composite lenses in an essentially common front plane, the frame having side sections extending proximally and positionable over ears of the user; and
    supplemental composite lenses positioned in the front section adjacent to the side sections, the supplemental lenses being in essentially parallel side planes perpendicular to the front plane, the supplemental composite lenses adapted to provide lateral vision free from the effects of laser and fluroscope radiation, the supplemental lenses having slightly different curves to compensate for the refractive index of the refractive glass.

9. The system (100) as set forth in claim 1 and further including:
    a frame (104) having a front section (106) receiving and supporting a pair of composite lenses (108) in an essentially common front plane, the frame having side sections (110) extending proximally and positionable over ears of the user; and
    hinges (114) in a vertical plane coupling the front and side sections.

10. The system (200) as set forth in claim 1 and further including:
    a frame (204) having a front section (206) receiving and supporting a pair of composite lenses (208) in an essentially common front plane, the frame having side sections (210) extending proximally and positionable over ears of the user; and
    hinges (214) in a horizontal plane coupling the front and side sections.

11. A laser-x radiation/laser combo protective eyewear system (10) for abating, through safety filtration, the harmful effects to eyes of a user from laser radiation and from radiation from fluoroscopy imaging procedures, the abating of the harmful radiation effects being done in a safe, convenient and economic manner, the system comprising, in combination:
    two primary lens elements (14), each primary lens element having a proximal face (16) and a planar distal face (18) and a central region (20) and a peripheral region (22), each primary lens element being fabricated of laser protective glass, the laser protective glass having laser glass protective ranges of 900 nm to 950 nm at 4+ OD and 80 percent visibility L-6 rating, and 950 nm to 1000 nm at 5+ OD and 80 percent visibility L-6 rating, 1000 nm to 2400 nm at 6+ OD and 80 percent visibility L-6 rating, 2750 nm to 10600 nm at 7+OD and 80 percent visibility L-6 rating, each primary lens adapted to protect the eyes of the user from harmful effects of laser radiation;
    two secondary lens elements (26), each secondary lens element having a proximal face (28) and a planar distal face (30) and a central region (32) and a peripheral region (34), each secondary lens element fabricated of lead oxide glass, the lead oxide glass having a lead content of a minimum of 0.75 percent lead plus or minus 5 percent in a 1.80 high-index rate of refraction, the secondary lens adapted to protect the eyes of the user from harmful effects of fluoroscopy radiation;
    each secondary lens element being operatively coupled to an associated primary lens element to form two lens laminates (38) with the distal face of each primary lens forming a planar interface (40) with each proximal face of an associated secondary lens;

each proximal face of each primary lens and each distal face of each secondary lens being ground to form two composite lenses (44) with a minimum prescription whereby each composite lens has a central region of an enlarged thickness and each composite lens has a peripheral region of a reduced thickness less than the thickness of the central extent;

a frame (48) having a front section (50) receiving and supporting a pair of composite lenses in an essentially common front plane, the frame having side sections (52) extending proximally and positionable over ears of the user, the composite lenses being positioned in the frame with the primary lens elements located proximally of the secondary lens elements; and supplemental composite lenses (56) positioned in the front section adjacent to the side sections, the supplemental lenses being in essentially parallel side planes perpendicular to the front plane, the supplemental composite lenses adapted to provide lateral vision free from the effects of laser and fluoroscope radiation, the supplemental lenses having slightly different curves to compensate for the refractive index of the refractive glass.

\* \* \* \* \*